United States Patent
Kwon et al.

(10) Patent No.: US 10,106,739 B2
(45) Date of Patent: Oct. 23, 2018

(54) LIQUID CRYSTAL COMPOSITION AND LIQUID CRYSTAL DISPLAY DEVICE COMPRISING THE SAME

(71) Applicant: Samsung Display Co., Ltd., Yongin-si, Gyeonggi-do (KR)

(72) Inventors: Sun Young Kwon, Seoul (KR); Fusayuki Takeshita, Seoul (KR); Keun Chan Oh, Cheonan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/091,371

(22) Filed: Apr. 5, 2016

(65) Prior Publication Data

US 2016/0348002 A1    Dec. 1, 2016

(30) Foreign Application Priority Data

May 29, 2015    (KR) .................... 10-2015-0076079

(51) Int. Cl.
   *C09K 19/30* (2006.01)
   *C07C 13/28* (2006.01)
   (Continued)

(52) U.S. Cl.
   CPC .......... *C09K 19/3048* (2013.01); *C07C 13/28* (2013.01); *C07C 22/00* (2013.01);
   (Continued)

(58) Field of Classification Search
   CPC ................................................. G02F 1/1341
   See application file for complete search history.

(56) References Cited

U.S. PATENT DOCUMENTS

2012/0261614 A1    10/2012 Goto et al.
2013/0248762 A1    9/2013 Hirschmann et al.

FOREIGN PATENT DOCUMENTS

EP    2594548 A1    5/2013
EP    2796922 A1    10/2014
(Continued)

OTHER PUBLICATIONS

Redolf et al. "Synthese neur potentiell fluessigkristalliner Verbindungen auf Bicyclohexyliden-Basis-Kristallstruktur des (Z)-3,10-Diphenyldispiro[5.0.5.1]tridecans" Journal of Chemical Research, vol. 10, Jun. 5, 1984, pp. 2910-2929.*

(Continued)

*Primary Examiner* — Chanceity N Robinson
(74) *Attorney, Agent, or Firm* — Cantor Colburn LLP

(57) ABSTRACT

A liquid crystal composition includes one or more compounds represented by Chemical Formula 1.

[Chemical Formula 1]

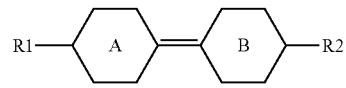

In Chemical Formula 1, (Continued)

are a cyclohexane or tetrahydropyran, and R1 and R2 are each independently hydrogen, a C1 to C8 alkyl group, a C2 to C8 alkenyl group, or a C1 to C8 alkoxy group.

14 Claims, 4 Drawing Sheets

(51) Int. Cl.
<table>
<tr><td>C07C 22/00</td><td>(2006.01)</td></tr>
<tr><td>C07C 23/18</td><td>(2006.01)</td></tr>
<tr><td>C07C 43/188</td><td>(2006.01)</td></tr>
<tr><td>C07C 43/192</td><td>(2006.01)</td></tr>
<tr><td>C07D 309/04</td><td>(2006.01)</td></tr>
<tr><td>G02F 1/1343</td><td>(2006.01)</td></tr>
<tr><td>C09K 19/06</td><td>(2006.01)</td></tr>
<tr><td>C09K 19/34</td><td>(2006.01)</td></tr>
<tr><td>C09K 19/12</td><td>(2006.01)</td></tr>
</table>

(52) U.S. Cl.
CPC ............ *C07C 23/18* (2013.01); *C07C 43/188* (2013.01); *C07C 43/192* (2013.01); *C07D 309/04* (2013.01); *C09K 19/062* (2013.01); *C09K 19/063* (2013.01); *C09K 19/3003* (2013.01); *G02F 1/134309* (2013.01); *C07C 2601/14* (2017.05); *C09K 2019/122* (2013.01); *C09K 2019/124* (2013.01); *C09K 2019/301* (2013.01); *C09K 2019/3004* (2013.01); *C09K 2019/305* (2013.01); *C09K 2019/3009* (2013.01); *C09K 2019/3016* (2013.01); *C09K 2019/3021* (2013.01); *C09K 2019/3027* (2013.01); *C09K 2019/3422* (2013.01)

(56) References Cited

FOREIGN PATENT DOCUMENTS

<table>
<tr><td>JP</td><td>07-069992 A</td><td>*</td><td>3/1995</td></tr>
<tr><td>KR</td><td>100716969</td><td></td><td>5/2005</td></tr>
<tr><td>KR</td><td>1020130110162</td><td></td><td>10/2013</td></tr>
<tr><td>KR</td><td>1020140014177</td><td></td><td>2/2014</td></tr>
<tr><td>KR</td><td>1020140043838</td><td></td><td>4/2014</td></tr>
</table>

OTHER PUBLICATIONS

English machine translation JP07-069992 A (Feb. 20, 2018).*
Shin-Tson Wu, et al., "Optimal operation temperature of liquid crystal modulators", Applied Optics, (1987), vol. 26, No. 16, p. 3441.
Extended European Search Report dated Oct. 27, 2016, of the corresponding European Patent Application No. 16171801.0.
Horst Redlof, et al., "Synthese neuer potentiell fussigkristalliner verbindungen auf Bicyclohexyliden-Basis-Kristallstruktur des (z)-3-10-Diphenyldispiro-[5.0.5.1]tridecans" Journal of Chemical Research, vol. 10, Jun. 5, 1984, pp. 2910-2929.

* cited by examiner

LIQUID CRYSTAL COMPOSITION AND LIQUID CRYSTAL DISPLAY DEVICE COMPRISING THE SAME

This application claims priority to Korean Patent Application No. 10-2015-0076079 filed on May 29, 2015, and all the benefits accruing therefrom under 35 U.S.C. § 119, the content of which in its entirety is herein incorporated by reference.

BACKGROUND

(a) Technical Field

The present invention relates to a liquid crystal composition and a liquid crystal display device including the same.

(b) Description of the Related Art

A liquid crystal display ("LCD") is a popular type of flat panel display. The liquid crystal display is capable of determining a direction of the liquid crystal molecules of the liquid crystal layer and controlling transmittance of light passing through the liquid crystal layer by applying a voltage to the field generating electrodes to generate an electric field in the liquid crystal layer.

The liquid crystal layer allows the liquid crystal display to achieve a desired image by controlling the transmittance of light. In particular, various characteristics are desirable for the liquid crystal displays, such as, low-voltage driving, high voltage holding ratio ("VHR"), a wide viewing angle, a wide operation temperature range, and high-speed response.

To obtain a high speed response characteristic for a liquid crystal display, it is desirable to improve the physical properties of the liquid crystal layer, such as, rotational viscosity, refractive index, and elastic coefficient.

SUMMARY

The present invention provides a liquid crystal composition capable of achieving a high speed response characteristic and low temperature stability, and a display device including the same.

In exemplary embodiments, a liquid crystal composition includes one or more compounds represented by Chemical Formula 1.

[Chemical Formula 1]

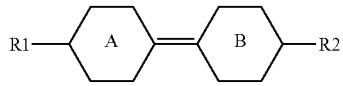

In Chemical Formula 1,

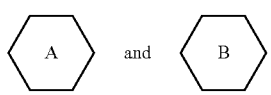

are each a cyclohexane or tetrahydropyran.

In Chemical Formula 1, R1 and R2 are independently hydrogen, a C1 to C8 alkyl group, a C2 to C8 alkenyl group, or a C1 to C8 alkoxy group.

In one exemplary embodiment, in the compound of Chemical Formula 1, one or more hydrogen in R1 and R2 may be substituted with fluorine (F), one or more —$CH_2$— group in R1 and R2 may be substituted with —$OCH_2$—, —$CF_2$—, and —$OCF_2$—, or one or more —$CH_3$ group in R1 and R2 may be substituted with —$CF_3$ or —$OCF_3$.

In an exemplary embodiment, in the compound of Chemical Formula 1, one or more hydrogen in

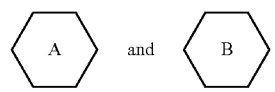

may be substituted with F, or one or more —$CH_2$— group in

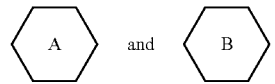

may be substituted with one of —O— or —$CF_2$—.

In an exemplary embodiment, the compound represented by Chemical Formula 1 may be at least one selected from Chemical Formulas 1-1 to 1-9.

[Chemical Formula 1-1]

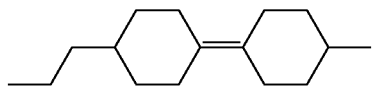

[Chemical Formula 1-2]

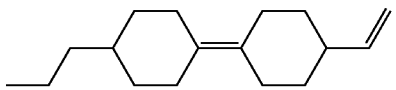

[Chemical Formula 1-3]

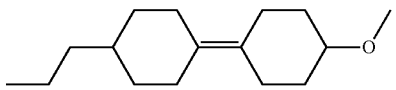

[Chemical Formula 1-4]

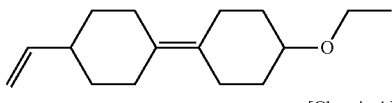

[Chemical Formula 1-5]

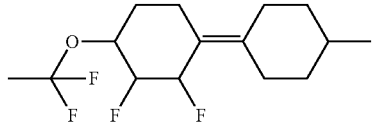

[Chemical Formula 1-6]

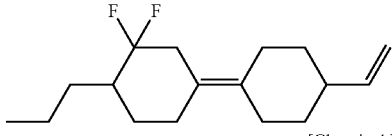

[Chemical Formula 1-7]

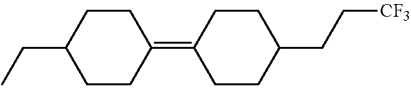

[Chemical Formula 1-8]

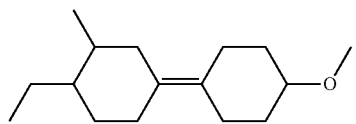

[Chemical Formula 1-9]

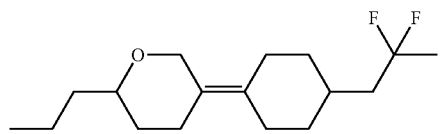

In an exemplary embodiment, the compound represented by Chemical Formula 1 may be present in an amount of about 1 wt % to about 40 wt % based on the entire weight of the liquid crystal composition.

In an exemplary embodiment, the liquid crystal composition may further include at least one compound selected from Chemical Formulas 2-1 to 2-8.

[Chemical Formula 2-1]

[Chemical Formula 2-2]

[Chemical Formula 2-3]

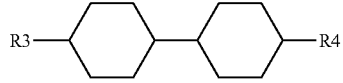

[Chemical Formula 2-4]

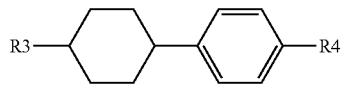

[Chemical Formula 2-5]

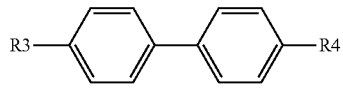

[Chemical Formula 2-6]

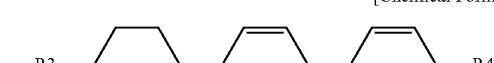

[Chemical Formula 2-7]

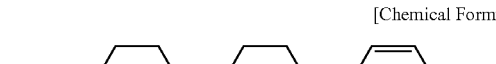

[Chemical Formula 2-8]

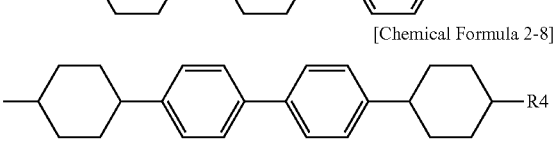

In Chemical Formulas 2-1 to 2-8, R3 and R4 may be independently a hydrogen, a C1 to C8 alkyl group, a C2 to C8 alkenyl group, or a C1 to C8 alkoxy group.

In an exemplary embodiment, one or more hydrogen in R3 and R4 may be substituted with F, one or more —CH$_2$— group in R3 and R4 may be substituted with —OCH$_2$—, —CF$_2$—, and —OCF$_2$—, or one or more —CH$_3$ group in R3 and R4 may be substituted with —CF$_3$ or —OCF$_3$.

In an exemplary embodiment, the compound selected from Chemical Formulas 2-1 to 2-8 may be present in an amount of about 2 wt % to about 40 wt % based on the entire weight of the liquid crystal composition.

In an exemplary embodiment, the liquid crystal composition may further include at least one compound selected from Chemical Formulas 3-1 to 3-12.

[Chemical Formula 3-1]

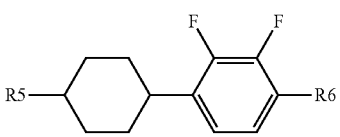

[Chemical Formula 3-2]

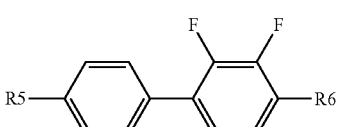

[Chemical Formula 3-3]

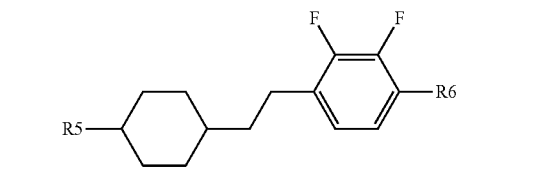

[Chemical Formula 3-4]

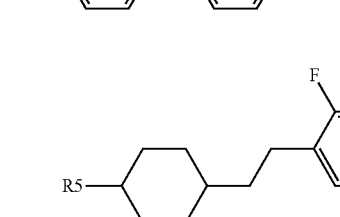

[Chemical Formula 3-5]

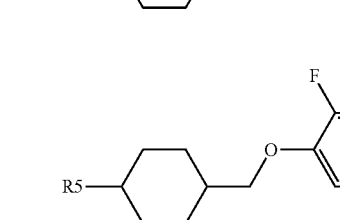

[Chemical Formula 3-6]

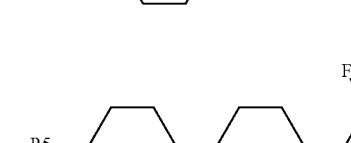

[Chemical Formula 3-7]

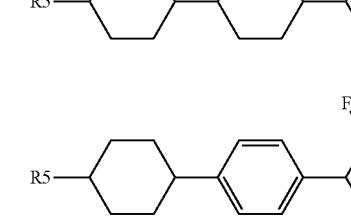

[Chemical Formula 3-8]

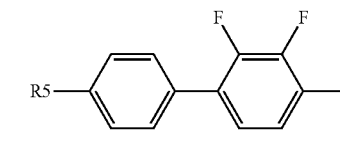

[Chemical Formula 3-9]

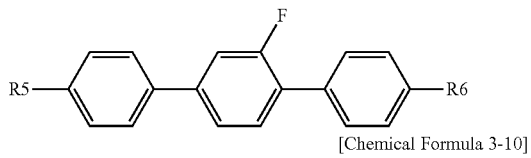

[Chemical Formula 3-10]

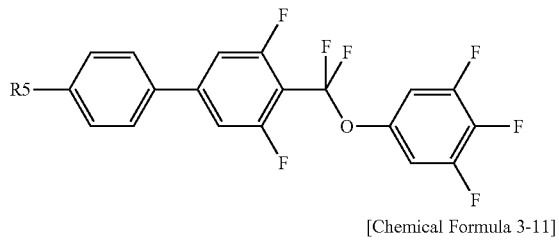

[Chemical Formula 3-11]

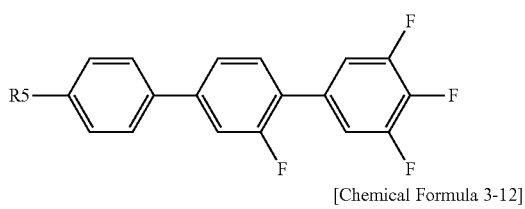

[Chemical Formula 3-12]

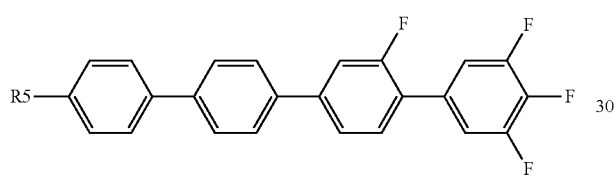

In Chemical Formulas 3-1 to 3-12, R5 and R6 may be independently hydrogen, a C1 to C8 alkyl group, a C2 to C8 alkenyl group, or a C1 to C8 alkoxy group.

In an exemplary embodiment, at least one hydrogen in R5 and R6 may be substituted with fluorine.

In an exemplary embodiment, the compound of Chemical Formula 3-1 to 3-12 may be present in an amount of about 2 wt % to about 30 wt % based on the entire weight of the liquid crystal composition.

In exemplary embodiments, a liquid crystal display includes a first insulation substrate including a pixel electrode; a second insulation substrate facing the first insulation substrate and including a common electrode; and a liquid crystal layer positioned between the first insulation substrate and the second insulation substrate, wherein the liquid crystal layer includes one or more compounds represented by Chemical Formula 1.

[Chemical Formula 1]

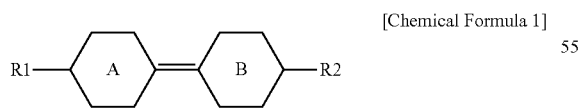

In Chemical Formula 1,

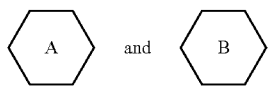

are independently a cyclohexane or tetrahydropyran.

In Chemical Formula 1, R1 and R2 are independently hydrogen, a C1 to C8 alkyl group, a C2 to C8 alkenyl group, or a C1 to C8 alkoxy group.

In an exemplary embodiment, in the compound of Chemical Formula 1, one or more hydrogen in R1 and R2 is substituted with F, one or more —CH$_2$— group in R1 and R2 is substituted with —OCH$_2$—, —CF$_2$—, or —OCF$_2$—, or one or more —CH$_3$ group in R1 and R2 is substituted with —CF$_3$ or —OCF$_3$.

In an exemplary embodiment, in the compound of Chemical Formula 1, one or more hydrogen in

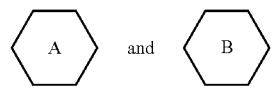

is substituted with F, or one or more —CH$_2$— group is substituted with one of —O— or —CF$_2$—.

In an exemplary embodiment, the compound represented by Chemical Formula 1 is at least one compound selected from Chemical Formulas 1-1 to 1-9.

[Chemical Formula 1-1]

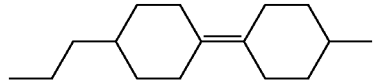

[Chemical Formula 1-2]

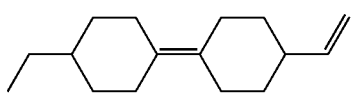

[Chemical Formula 1-3]

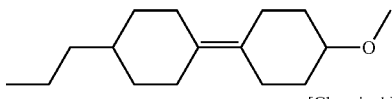

[Chemical Formula 1-4]

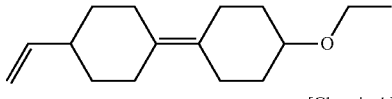

[Chemical Formula 1-5]

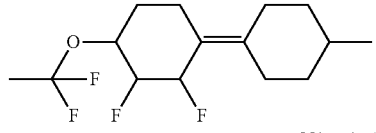

[Chemical Formula 1-6]

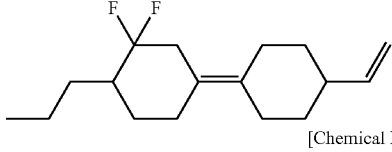

[Chemical Formula 1-7]

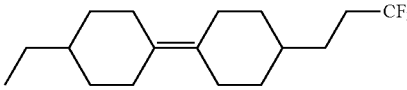

[Chemical Formula 1-8]

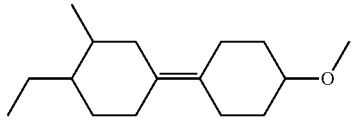

[Chemical Formula 1-9]

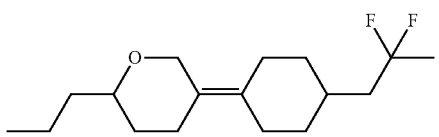

In an exemplary embodiment, the compound represented by Chemical Formula 1 is present in an amount of about 1 wt % to about 40 wt % based upon the entire weight of the liquid crystal composition.

In an exemplary embodiment, the liquid crystal layer further includes at least one compound selected from Formulas 2-1 to 2-8.

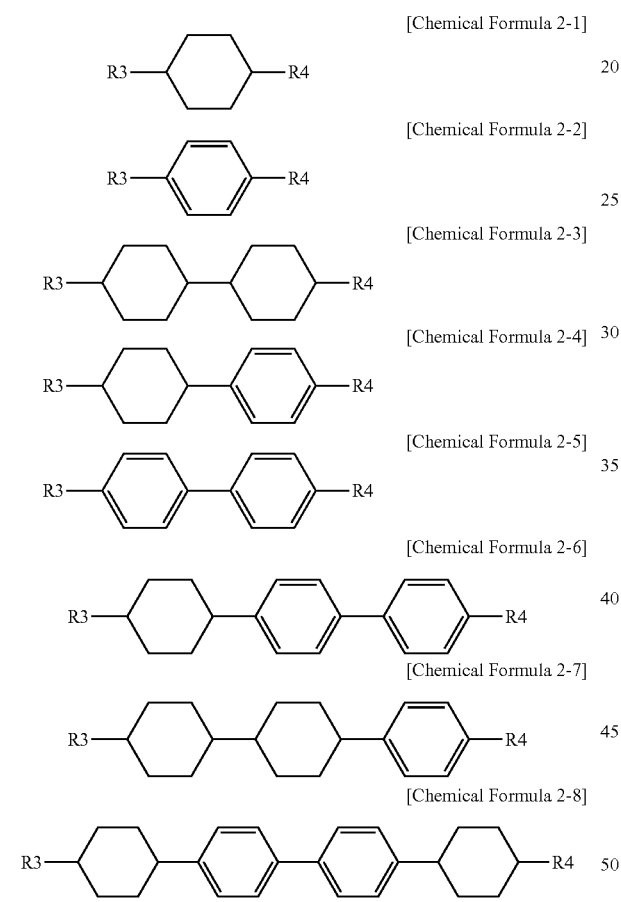

[Chemical Formula 2-1]

[Chemical Formula 2-2]

[Chemical Formula 2-3]

[Chemical Formula 2-4]

[Chemical Formula 2-5]

[Chemical Formula 2-6]

[Chemical Formula 2-7]

[Chemical Formula 2-8]

In Chemical Formula 2-1 to 2-8, R3 and R4 are independently hydrogen, a C1 to C8 alkyl group, a C2 to C8 alkenyl group, or a C 1 to C8 alkoxy group.

In an exemplary embodiment, one or more hydrogen in R3 and R4 is substituted with F, one or more —$CH_2$— group in R3 and R4 is substituted with one among —$OCH_2$—, —$CF_2$—, and —$OCF_2$—, or one or more —$CH_3$ group in R3 and R4 is substituted with —$CF_3$ or —$OCF_3$.

In an exemplary embodiment, compound selected from Chemical Formulas 2-1 to 2-8 is present in an amount of about 2 wt % to about 40 wt % based on the entire weight of the liquid crystal composition.

In an exemplary embodiment, the liquid crystal layer further includes at least one compound selected from Chemical Formulas 3-1 to 3-12.

[Chemical Formula 3-1]

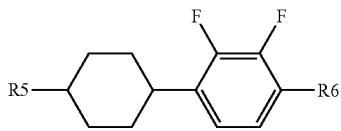

[Chemical Formula 3-2]

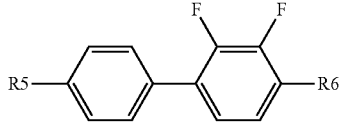

[Chemical Formula 3-3]

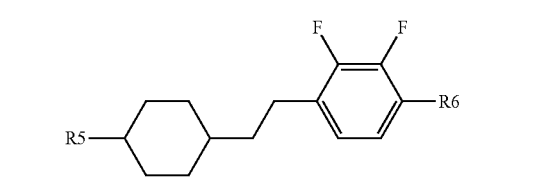

[Chemical Formula 3-4]

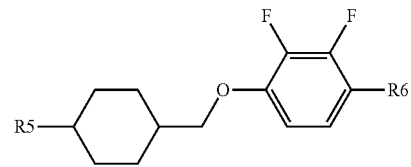

[Chemical Formula 3-5]

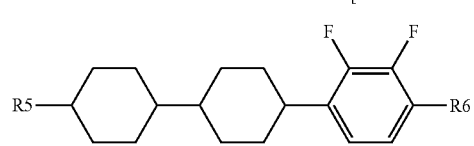

[Chemical Formula 3-6]

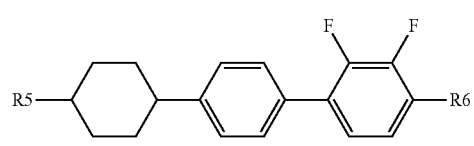

[Chemical Formula 3-7]

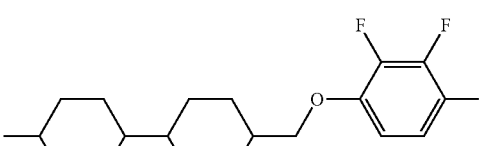

[Chemical Formula 3-8]

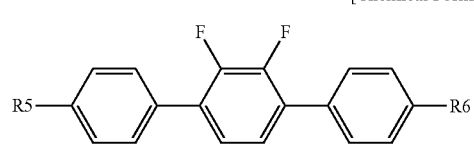

[Chemical Formula 3-9]

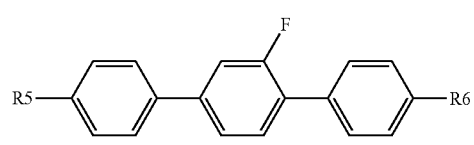

-continued

[Chemical Formula 3-10]

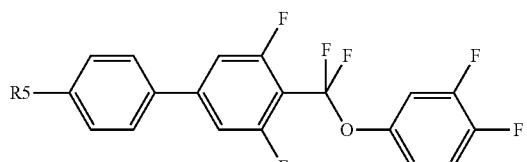

[Chemical Formula 3-11]

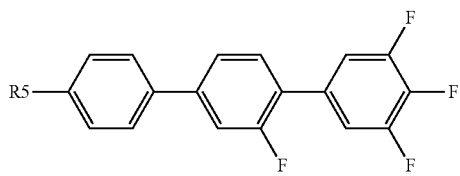

[Chemical Formula 3-12]

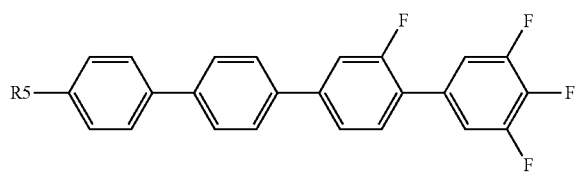

In Chemical Formula 3-1 to 3-12, R5 and R6 are independently hydrogen, a C1 to C8 alkyl group, a C2 to C8 alkenyl group, or a C1 to C8 alkoxy group.

In an exemplary embodiment, at least one hydrogen in R5 and R6 is substituted with fluorine.

In an exemplary embodiment, the compound selected from Chemical Formulas 3-1 to 3-12 is present in an amount of about 2 wt % to about 30 wt % based on the entire weight of the liquid crystal composition.

In an exemplary embodiment, the pixel electrode may include a cross-shape stem and a minute branch extending from the cross-shape stem in 4 diagonal directions.

As described above, an exemplary embodiment of the present invention provides a liquid crystal composition including a compound in which the cyclohexane is connected with a double bond, along with a liquid crystal display applied with the same, thereby improving the performance of the liquid crystal display.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Figure 1:
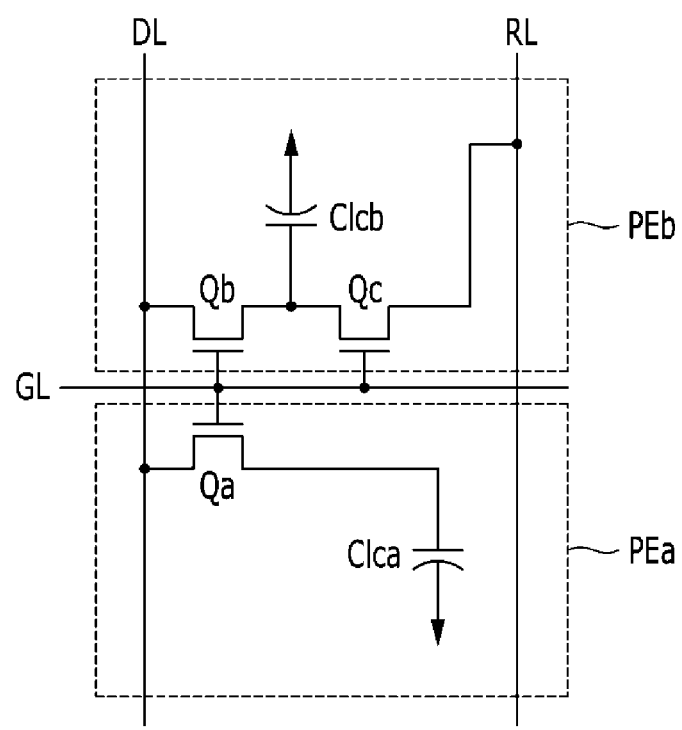
FIG. 1 is an equivalent circuit diagram of one pixel of an exemplary embodiment of a liquid crystal display according to the present invention.

The present invention will be described more fully hereinafter with reference to the accompanying drawings, in which various exemplary embodiments are shown. As those skilled in the art would realize, the described embodiments may be modified in various different ways, all without departing from the spirit or scope of the present invention. Rather, these embodiments are provided so that this disclosure will be thorough and complete, and will fully convey the scope of the invention to those skilled in the art. Like reference numerals refer to like elements throughout.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Exemplary embodiments of a liquid crystal composition and a liquid crystal display including the liquid crystal composition are described with reference to the accompanying drawings.

In an exemplary embodiment, a liquid crystal composition includes one or more compounds represented by Chemical Formula 1.

[Chemical Formula 1]

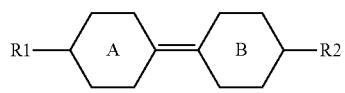

In Chemical Formula 1,

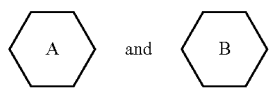

are each cyclohexane or tetrahydropyran.

In Chemical Formula 1, R1 and R2 are independently hydrogen, a C1 to C8 alkyl group, C2 to C8 alkenyl group, or a C1 to C8 alkoxy group.

Also, one or more hydrogen included in

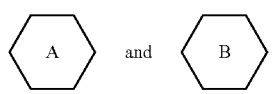

of Chemical Formula 1 may be substituted with F, or one or more —CH$_2$— group in

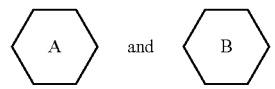

may be substituted with —O— or —CF$_2$—.

In Chemical Formula 1, one or more hydrogen in R1 and R2 may be substituted with F, one or more —CH$_2$— group in R1 and R2 may be substituted with —OCH$_2$—, —CF$_2$—, or —OCF$_2$—, or one or more —CH$_3$ group in R1 and R2 may be substituted with —CF$_3$ or —OCF$_3$.

The compound of Chemical Formula 1 may be selected from Chemical Formulas 1-1 to Chemical Formula 1-9.

[Chemical Formula 1-1]

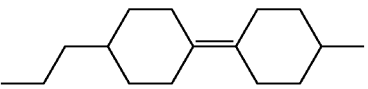

[Chemical Formula 1-2]

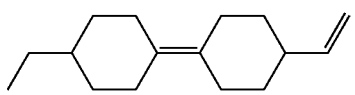

[Chemical Formula 1-3]

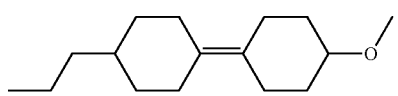

[Chemical Formula 1-4]

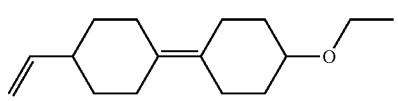

[Chemical Formula 1-5]

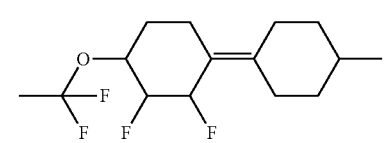

[Chemical Formula 1-6]

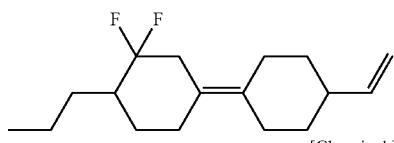

[Chemical Formula 1-7]

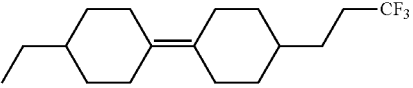

[Chemical Formula 1-8]

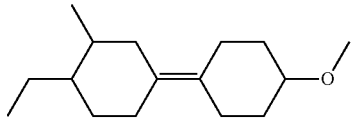

[Chemical Formula 1-9]

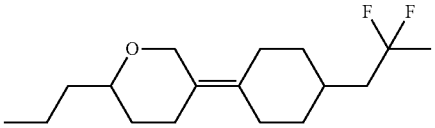

A process of manufacturing the compound represented by Chemical Formula 1 may include the steps illustrated below.

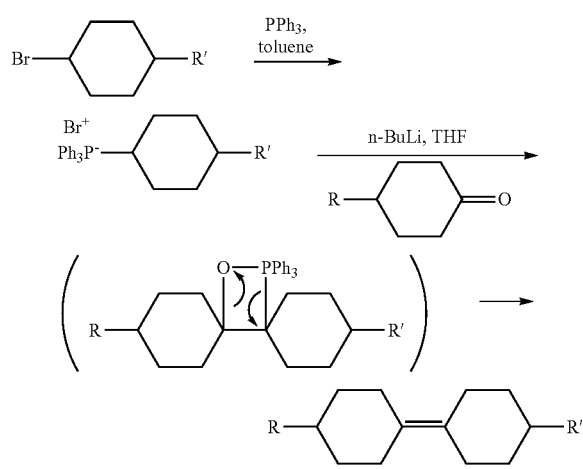

However, the above manufacturing process is only one possible example, and the compound of Chemical Formula 1 may also be manufactured by other manufacturing processes.

In an exemplary embodiment, the liquid crystal composition may include about 1 wt % to about 40 wt % of the compound represented by Chemical Formula 1

In one exemplary embodiment, the liquid crystal composition may additionally include at least one compound selected from Chemical Formulas 2-1 to 2-8.

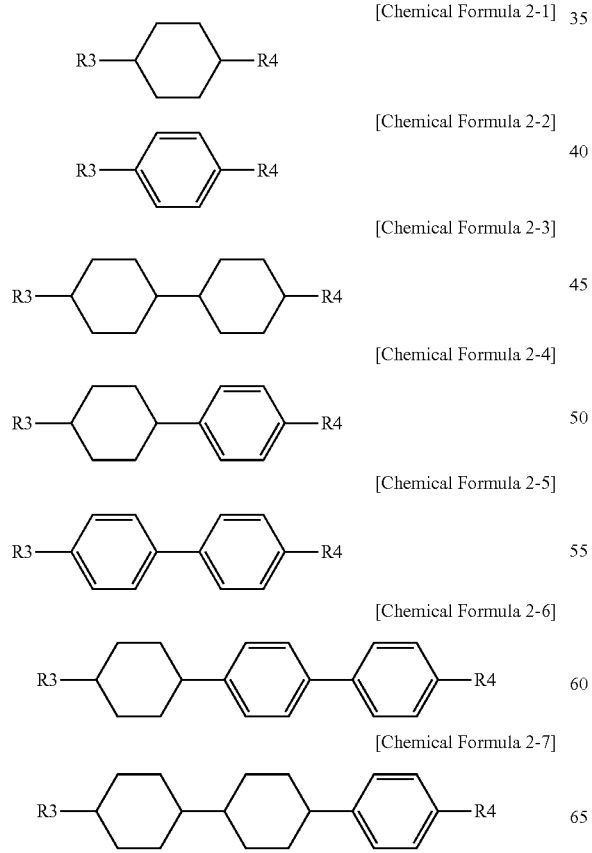

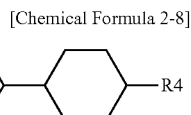

In Chemical Formulas 2-1 to 2-8, R3 and R4 are independently hydrogen, a C1 to C8 alkyl group, a C2 to C8 alkenyl group, or a C1 to C8 alkoxy group.

In Chemical Formulas 2-1 to 2-8, at least one hydrogen in R3 and R4 may be substituted with F, one or more —CH2— group in R3 and R4 may be substituted with —OCH2—, —CF2—, or —OCF2—, or one or more —CH3 group in R3 and R4 may be substituted with —CF3 or —OCF3.

Also, in the liquid crystal composition of the present invention, the compound of Chemical Formula 2-1 to 2-8 may be present in an amount of about 2 wt % to about 40 wt % based on the entire weight of the liquid crystal composition.

The liquid crystal composition of the present invention may additionally include at least one compound selected from Chemical Formulas 3-1 to 3-12.

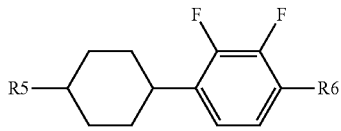

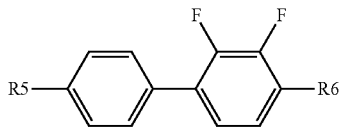

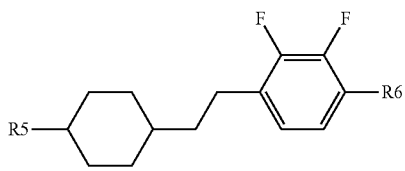

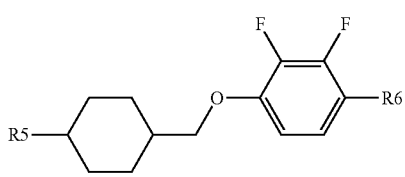

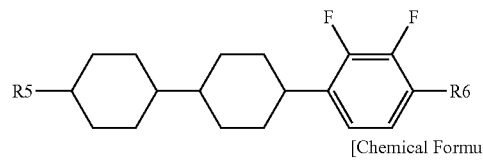

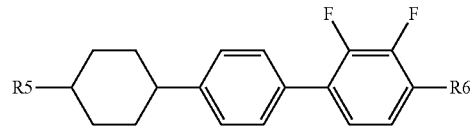

-continued

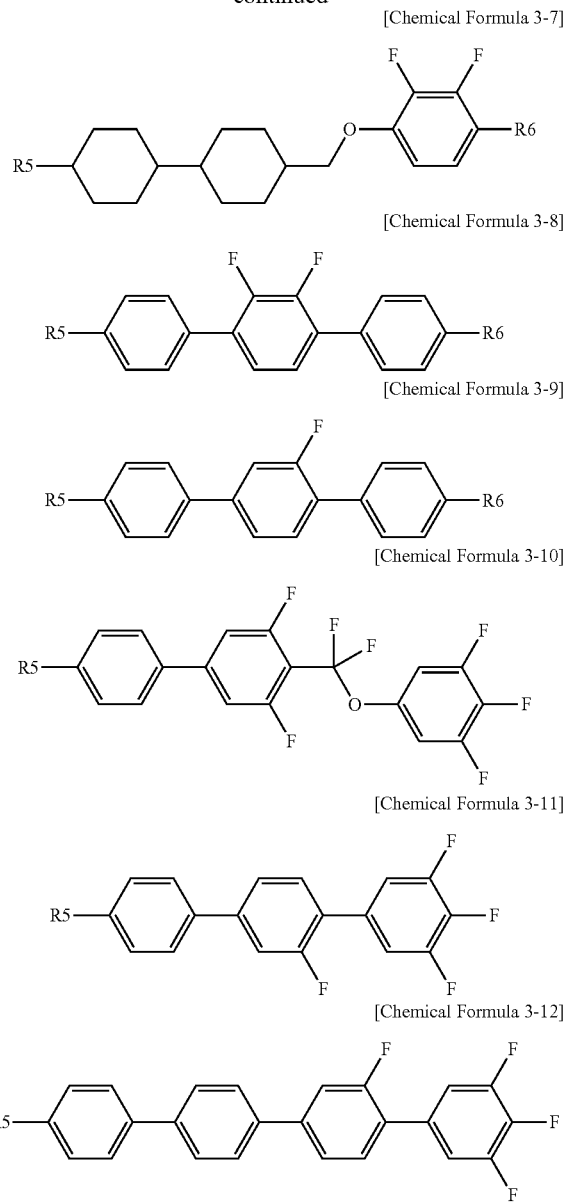

[Chemical Formula 3-7]
[Chemical Formula 3-8]
[Chemical Formula 3-9]
[Chemical Formula 3-10]
[Chemical Formula 3-11]
[Chemical Formula 3-12]

In Chemical Formula 3-1 to 3-12, R5 and R6 are independently hydrogen, a C1 to C8 alkyl group, a C2 to C8 alkenyl group, or a C1 to C8 alkoxy group.

Also, at least one hydrogen in R5 and R6 may be substituted with fluorine.

In the liquid crystal composition of the present invention, a content of the compound of Chemical Formula 3-1 to 3-12 may be about 2 wt % to about 30 wt % based on the entire weight of the liquid crystal composition.

As described above, the exemplary liquid crystal composition of the present invention includes the compound represented by Chemical Formula 1.

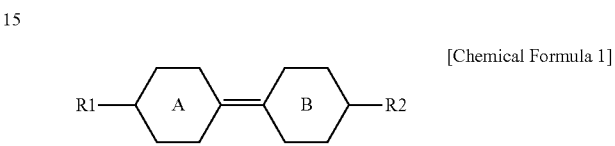

[Chemical Formula 1]

In this case, the compound represented by Chemical Formula 1 is formed of two cyclohexane rings connected with a double bond and both having terminal groups. Since the double bond positioned between the two cyclohexane rings is covered by the surrounding hydrogen atoms, the reactivity of the compound is not high and a relatively stable state may be maintained.

A Comparative Example is a compound having two cyclohexane rings connected by a single bond. The exemplary liquid crystal composition which includes the compound of Chemical Formula 1 in which two cyclohexane rings are connected by the double bond, was compared to a liquid crystal composition including a compound in which the two cyclohexane rings are connected by a single bond. It was surprisingly found that a liquid crystal composition including the compound of Chemical Formula 1 had improved low temperature stability and low viscosity, thereby improving response speed.

Table 1 shows a comparison of the physical properties of the compound of the present invention (Exemplary Embodiment) in which two cyclohexane rings are connected by a double bond and the compound of the Comparative Example in which two cyclohexane rings are connected by a single bond. The physical properties of the compounds (molecular weight, dipole moment D, refractive anisotropy $\Delta n$, rotation viscosity $\gamma 1$, and low temperature stability) were measured.

TABLE 1

| Division | Chemical Formula | M.W. | Dipole moment (D) | $\Delta n$ | $\gamma 1$ (mPas) | Low temperature stability |
|---|---|---|---|---|---|---|
| Comparative Example | | 236.44 | 0.007 | 0.03 | 16 | Δ |
| | | 234.43 | 0.223 | 0.04 | 16 | ○ |
| Exemplary embodiment | | 234.43 | 0.008 | 0.04 | 15 | ○ |

TABLE 1-continued

| Division | Chemical Formula | M.W. | Dipole moment (D) | Δn | γ1 (mPas) | Low temperature stability |
|---|---|---|---|---|---|---|
| | (cyclohexane=cyclohexane with vinyl and ethyl substituents) | 232.41 | 0.237 | 0.05 | 14 | ◎ |

Referring to Table 1, for the liquid crystal composition including a compound having the cyclohexane core with the double bond (Exemplary Embodiment), the low temperature stability was improved while the same level of reliability was maintained as compared to the compound having the cyclohexane core with the conventional single bond. That is, the physical properties are excellent and low temperature stability is improved, such that the content in the liquid crystal composition may be increased.

Also, referring to Table 1, in the case of the liquid crystal composition of the Exemplary Embodiment, it was also shown that the rotational viscosity was reduced as compared to the Comparative Example. The reduction of the rotational viscosity is configured to contribute to the response speed, and in the case of the exemplary liquid crystal composition, the rotational viscosity is reduced such that the response speed of the liquid crystal composition may be improved.

Next, the physical properties of the liquid crystal composition according to the Comparative Example and the liquid crystal composition according to the Exemplary Embodiment of the present invention are compared.

Table 2 shows the composition of an Exemplary Embodiment 1 of a liquid crystal composition.

TABLE 2

| Compound No. | Structure of Liquid crystal molecule | Content (%) |
|---|---|---|
| 1 | vinyl-cyclohexane=cyclohexane-propyl | 20 |
| 2 | propyl-cyclohexane=cyclohexane-propyl | 14 |
| 3 | propyl-cyclohexane-(difluorophenyl)-OEt | 22 |
| 4 | propyl-cyclohexane-cyclohexane-(difluorophenyl)-OEt | 22 |
| 5 | propyl-cyclohexane-phenyl-(difluorophenyl)-OEt | 22 |

Table 3 shows the composition of a Comparative Example 1 of a liquid crystal composition.

TABLE 3

| Compound No. | Structure of Liquid crystal molecule | Content (%) |
|---|---|---|
| 6 | vinyl-cyclohexane-cyclohexane-propyl | 20 |

TABLE 3-continued

| Compound No. | Structure of Liquid crystal molecule | Content (%) |
|---|---|---|
| 7 | | 14 |
| 8 | | 22 |
| 9 | | 22 |
| 10 | | 22 |

Table 4 compares the physical properties of the liquid crystal composition of Exemplary Embodiment 1 having the composition of Table 2 with the physical properties of the liquid crystal composition of Comparative Example 1 having the composition of Table 3.

The physical properties that were measured include an isotropic phase transition temperature (Tni), a refractive anisotropy (Δn), a dielectric anisotropy (Δε), a rotation viscosity γ1, a low temperature stability (LTS), and a voltage holding rate (VHR).

TABLE 4

| physical properties | Tni (° C.) | Δn | Δε | γ1 (mPas) | LTS (low temperature stability at −20° C.) | VHR (UV 5J) |
|---|---|---|---|---|---|---|
| Exemplary Embodiment 1 | 78 | 0.096 | −5.1 | 157 | Good | 88.7 |
| Comparative Example 1 | 84 | 0.095 | −5 | 158 | No good | 88.5 |

Referring to Table 4, it was confirmed that the liquid crystal composition according to the Exemplary Embodiment 1 was equal to or better than the liquid crystal composition according to the Comparative Example 1 with respect to all physical properties except for Tni. In particular, in the liquid crystal composition according to Exemplary Embodiment 1, it was confirmed that the low temperature stability was significantly improved as compared to the liquid crystal composition of Comparative Example 1.

This is because the cyclohexane groups in compounds (compound Nos. 1 and 2 of Table 2) of the present invention are connected with a double bond, but the cyclohexane groups in the compounds (compound Nos. 6 and 7 of Table 3) of the Comparative Example 1 are connected with a single bond.

That is, in the case of the conventional liquid crystal composition of Comparative Example 1, the cyclohexane groups are connected with a single bond (compound Nos. 6 and 7 of Table 3). In this case, the low temperature stability of the compound is low, and therefore even when the liquid crystal composition is included in an excessive amount, since the low temperature stability is decreased, a sufficient amount of the compound may not be present in the liquid crystal composition.

However, in the Exemplary Embodiment 1 of the liquid crystal composition, the cyclohexane groups are connected with a double bond (compound Nos. 1 and 2 of Table 2). This compound has excellent low temperature stability. Thus, as shown in Tables 2 to 4, when the Exemplary Embodiment 1 liquid crystal composition including this compound is included in an excessive amount, the low temperature stability is even better than the liquid crystal composition of Comparative Example 1.

As such, the improved low temperature stability allows for easy storage and distribution of the liquid crystal composition, thereby improving its economic viability.

Also, the compounds 1 and 2 of Table 2 and the compounds 5 and 6 of Table 3, are compounds that decrease the viscosity of the liquid crystal composition and contribute to the reaction speed.

The response speed of the liquid crystal and the rotational viscosity of the liquid crystal are related as follows. That is, if a cell gap d of the liquid crystal is increased, the response speed of the liquid crystal is increased, and if the rotation viscosity γ1 is increased, the response speed of the liquid crystal is increased.

$$\tau_{off} \propto \frac{\gamma_1 d^2}{K_{33}}$$

Accordingly, in the liquid crystal display with the same cell gap, to increase the response speed of the liquid crystal, it is important to decrease rotation viscosity.

In this case, as shown in Table 1, the compounds of the Exemplary embodiment have a lower rotational viscosity than the compounds of the Comparative Example. Accordingly, the response speed of the liquid crystal may be decreased.

Also, as described above, the liquid crystal composition according to the exemplary embodiment of the present invention may include a greater range of the compound contributing to the reaction speed. As described above, it is for this reason that the compound of Chemical Formula 1 of the present invention includes the cyclohexane groups connected with a double bond such that the low temperature stability is excellent, and the low temperature stability of the liquid crystal composition may be maintained even if an excessive amount of the compound is included.

That is, in an exemplary embodiment the liquid crystal composition according to the present invention includes the compound in which the cyclohexane groups are connected with a double bond such that the low temperature stability is excellent and the reaction speed is also improved as compared to the liquid crystal composition according to the conventional Comparative Example 1.

Next, in an exemplary embodiment, a liquid crystal display applied with the liquid crystal composition according to the present invention will be described.

However, the structure of the described liquid crystal display is only one example and the exemplary embodiment of the liquid crystal display may be clearly used without being limited to the case of a vertical alignment ("VA") mode liquid crystal display.

First, an arrangement and a driving method of a signal line and a pixel of the liquid crystal display of the present invention will be described with reference to FIG. 1. FIG. 1 is an equivalent circuit diagram for one pixel of a liquid crystal display according to an exemplary embodiment of the present invention.

Referring to FIG. 1, in an exemplary embodiment, one pixel PX of the liquid crystal display includes: a plurality of signal lines, including a gate line GL for transferring a gate signal, a data line DL for transferring a data signal, and a voltage division reference voltage line RL for transferring a voltage division reference voltage; first, second, and third switching elements Qa, Qb, and Qc; and first and second liquid crystal capacitors Clca and Clcb connected to the plurality of signal lines.

The first and second switching elements Qa and Qb are connected to the gate line GL and the data line DL, respectively, and the third switching element Qc is connected to the output terminal of the second switching element Qb and to the voltage division reference voltage line RL.

The first switching element Qa and the second switching element Qb are three-terminal elements, such as a thin film transistor. Control terminals thereof are connected to the gate line GL, input terminals thereof are connected to the data line DL, an output terminal of the first switching element Qa is connected to a first liquid crystal capacitor Clca, and an output terminal of the second switching element Qb is connected to a second liquid crystal capacitor Clcb and an input terminal of the third switching element Qc.

The third switching element Qc is also a three-terminal element, such as a thin film transistor, and the control terminal thereof is connected to the gate line GL, the input terminal thereof is connected to the second liquid crystal capacitor Clcb, and an output terminal thereof is connected to the voltage division reference voltage line RL.

When a gate-on signal is applied to the gate line GL, the first switching element Qa, the second switching element Qb, and the third switching element Qc connected to the gate line GL are turned on. Accordingly, a data voltage applied to the data line DL is applied to a first subpixel electrode PEa and a second subpixel electrode PEb through the turned-on first switching element Qa and second switching element Qb. In this case, the data voltages applied to the first subpixel electrode PEa and the second subpixel electrode PEb are the same, and the first liquid crystal capacitor Clca and the second liquid crystal capacitor Clcb are charged to the same value as the difference between the common voltage and the data voltage. Similarly, the voltage charged in the second liquid crystal capacitor Clcb is divided through the turned-on third switching element. Accordingly, the voltage value charged in the second liquid crystal capacitor Clcb is decreased by the difference between the common voltage and the voltage division reference voltage. That is, the voltage charged in the first liquid crystal capacitor Clca is higher than a voltage charged in the second liquid crystal capacitor Clcb.

As described above, the voltage charged in the first liquid crystal capacitor Clca and the voltage charged in the second liquid crystal capacitor Clcb are different from each other. Since the voltage of the first liquid crystal capacitor Clca and the voltage of the second liquid crystal capacitor Clcb are different from each other, inclination angles of liquid crystal molecules in the first subpixel and the second subpixel become different from each other, thus luminance of the two subpixels also become different from each other. Accordingly, when the voltage of the first liquid crystal capacitor Clca and the voltage of the second liquid crystal capacitor Clcb are appropriately adjusted, an image viewed from the side may be as close as possible to an image viewed from the front, thereby improving side visibility.

In the illustrated exemplary embodiment (FIG. 1), in order to make the voltage charged in the first liquid crystal capacitor Clca and the voltage charged in the second liquid crystal capacitor Clcb different from each other, the liquid crystal display includes the third switching element Qc connected to the second liquid crystal capacitor Clcb and the voltage division reference voltage line RL. However, in another exemplary embodiment of a liquid crystal display according to the present invention, the second liquid crystal capacitor Clcb may be connected to a step-down capacitor. In particular, the liquid crystal display includes the third switching element Qc including a first terminal connected to a step-down gate line, a second terminal connected to the second liquid crystal capacitor Clcb, and a third terminal connected to the step-down capacitor, and a portion of the amount of charge charged in the second liquid crystal capacitor Clcb is charged in the step-down capacitor, so that the charging voltages between the first liquid crystal capacitor Clcb and the second liquid crystal capacitor Clcb may be set differently. Further, in yet another exemplary embodiment of a liquid crystal display according to the present invention, the first liquid crystal capacitor Clca and the second liquid crystal capacitor Clcb are connected to different data lines and receive different data voltages, thus the charging voltages between the first liquid crystal capacitor Clca and the second liquid crystal capacitor Clcb may be set differently. In addition, the charging voltages between the first liquid crystal capacitor Clca and the second liquid crystal capacitor Clcb may be set differently by various other methods.

The arrangement of the first substrate and the second substrate of the liquid crystal display of the present invention will be described with reference to FIG. 2 to FIG. 4.

Figure 2:
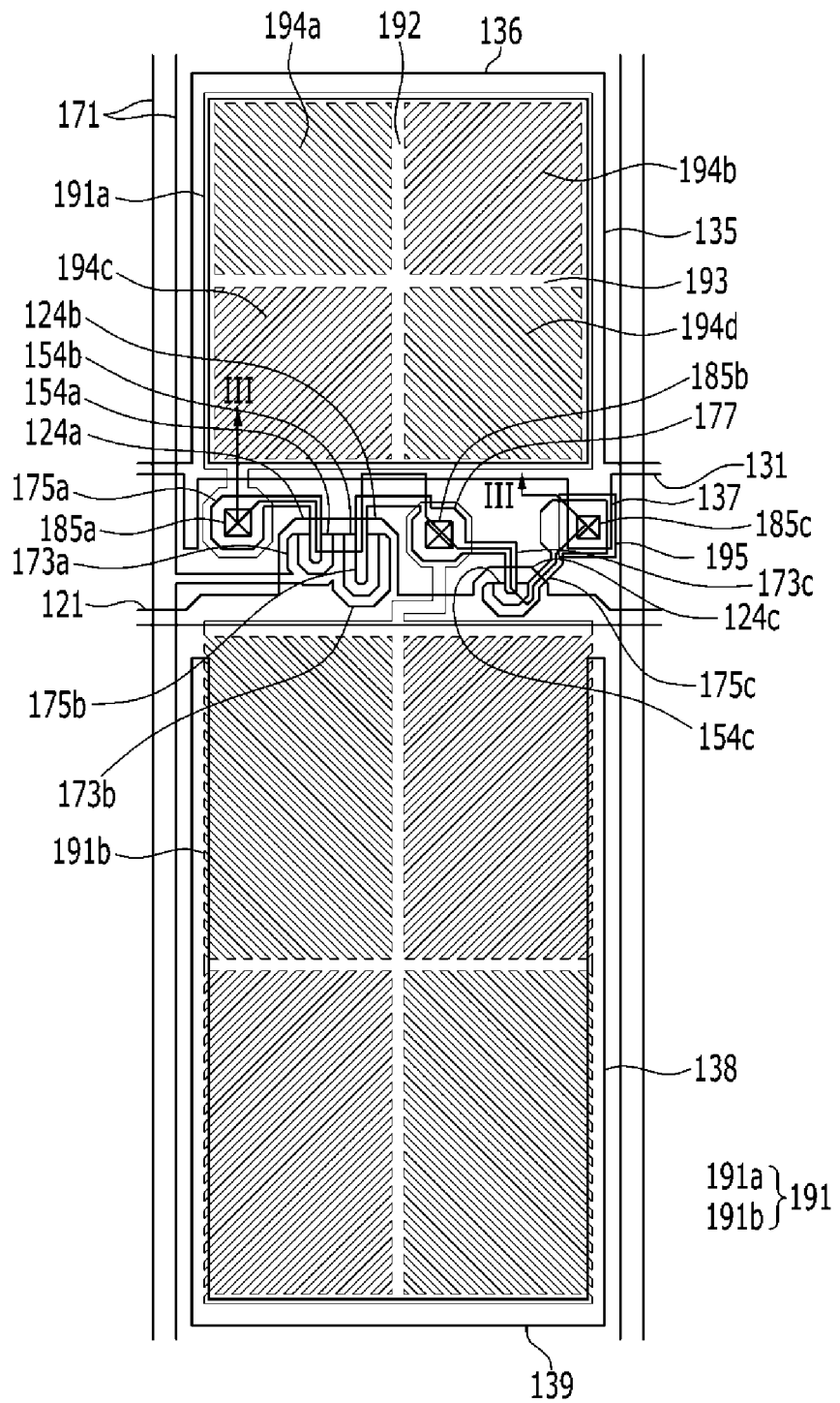
FIG. 2 is a plan view of an exemplary embodiment of a liquid crystal display according to the present invention.
Figure 3:
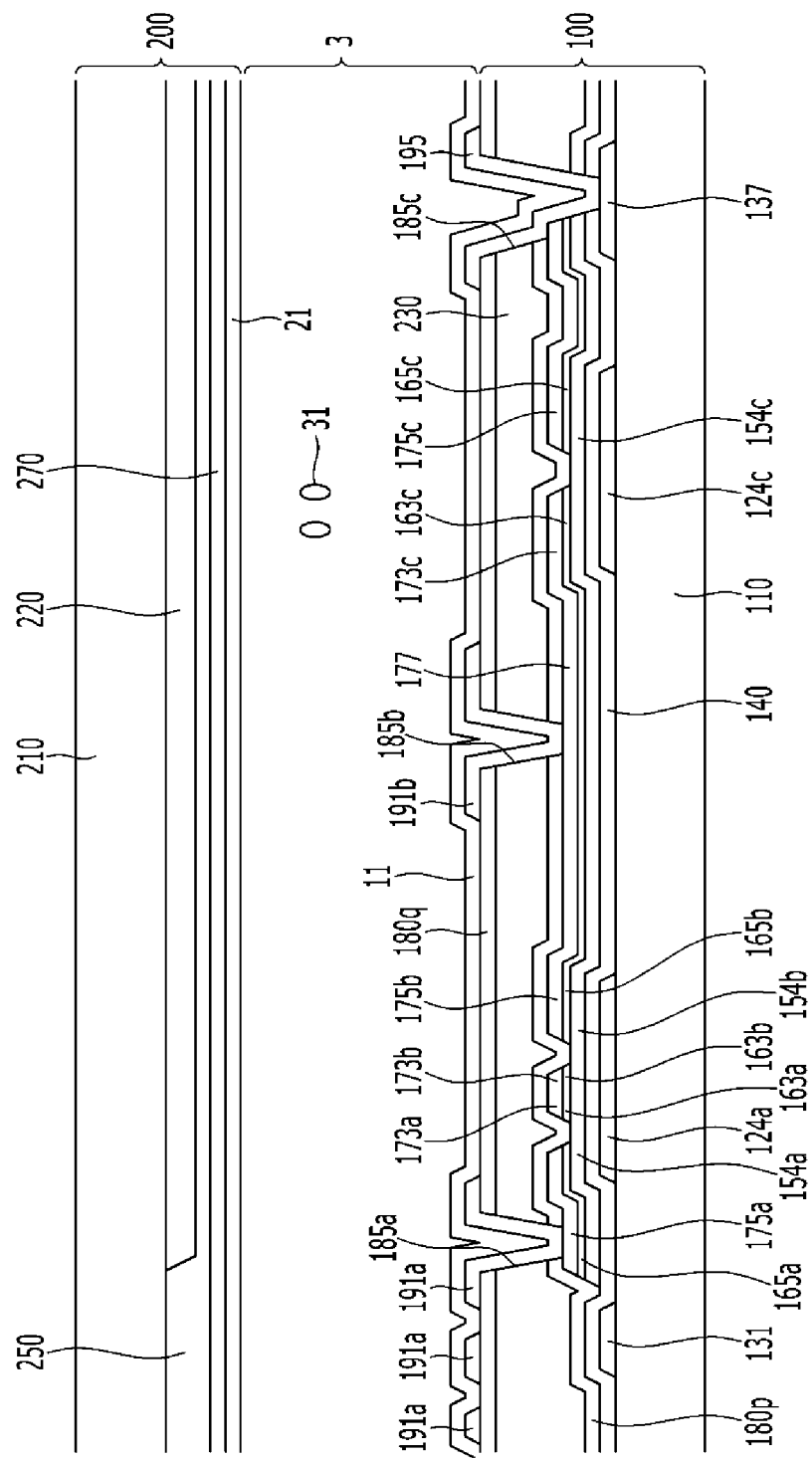
FIG. 3 is a cross-sectional view of the liquid crystal display of FIG. 2 taken along line IV-IV.

FIG. 2 is a plan view of an exemplary embodiment of a liquid crystal display according to the present invention, and FIG. 3 is a cross-sectional view of the liquid crystal display of FIG. 2 taken along line IV-IV. FIG. 4 is a top plan view of an exemplary embodiment of a basic region of a pixel electrode in a lower panel according to the present invention.

First, the lower panel 100 will be described.

A gate conductor including a gate line 121 and a voltage division reference voltage line 131 are formed on an insulating substrate 110. The insulating substrate 110 is formed of transparent glass, plastics, or the like.

The gate line 121 includes a first gate electrode 124a, a second gate electrode 124b, a third gate electrode 124c, and a wide end portion (not illustrated) for connection to another layer or an external driving circuit.

The voltage division reference voltage line 131 includes first storage electrodes 135 and 136, and a reference electrode 137. Second storage electrodes 138 and 139, which are not connected to the voltage division reference voltage line 131, but which overlap the second subpixel electrode 191b, are positioned on the lower panel 100.

A gate insulating layer 140 is formed on the gate line 121 and the voltage division reference voltage line 131.

A first semiconductor 154a, a second semiconductor 154b, and a third semiconductor 154c are formed on the gate insulating layer 140.

A plurality of ohmic contacts 163a, 165a, 163b, 165b, 163c, and 165c are formed on the semiconductors 154a, 154b, and 154c.

A plurality of data lines 171 including a first source electrode 173a and a second source electrode 173b, and data conductors including a first drain electrode 175a, a second drain electrode 175b, a third source electrode 173c, and a third drain electrode 175c are formed on the ohmic contacts 163a, 165a, 163b, 165b, 163c, and 165c, and the gate insulating layer 140.

The data conductors, as well as the semiconductors and the ohmic contacts positioned under the data conductors, may be simultaneously formed by using one mask.

The data line 171 includes a wide end portion (not illustrated) for connection with another layer or an external driving circuit.

The first gate electrode 124a, the first source electrode 173a, and the first drain electrode 175a form a first thin film transistor Qa together with the first semiconductor 154a, and a channel of the thin film transistor is formed on the semiconductor 154a between the first source electrode 173a and the first drain electrode 175a. Similarly, the second gate electrode 124b, the second source electrode 173b, and the second drain electrode 175b form a second thin film transistor Qb together with the second semiconductor 154b, and a channel of the thin film transistor is formed on the semiconductor 154b between the second source electrode 173b and the second drain electrode 175b. The third gate electrode 124c, the third source electrode 173c, and the third drain electrode 175c form a third thin film transistor Qc together with the third semiconductor 154c, and a channel of the thin film transistor is formed on the semiconductor 154c between the third source electrode 173c and the third drain electrode 175c.

The second drain electrode 175b is connected with the third source electrode 173c, and includes an extended portion 177 that widely extends.

A first passivation layer 180p is formed on the data conductors 171, 173c, 175a, 175b, and 175c and exposed portions of the semiconductors 154a, 154b, and 154c. The first passivation layer 180p may include an inorganic insulating layer, such as a silicon nitride or a silicon oxide. The first passivation layer 180p may prevent a pigment of a color filter 230 from flowing into the exposed portions of the semiconductors 154a, 154b, and 154c.

The color filter 230 is formed on the first passivation layer 180p. The color filter 230 extends in a vertical direction along two adjacent data lines. A first light blocking member 220 is positioned on the first passivation layer 180p, an edge of the color filter 230, and the data line 171.

Alternatively, the color filter 230 may not be formed on the lower display panel 100, but rather may be on the upper display panel 200.

A second passivation layer 180q is formed on the color filter 230. The second passivation layer 180q may include an inorganic insulating layer such as a silicon nitride or a silicon oxide. The second passivation layer 180q prevents lifting of the color filter 230 and reduces pollution of the liquid crystal layer 3 due to an organic material such as a solvent flowing from the color filter 230, thereby preventing defects such as afterimage, which may be generated when a screen is driven.

A first contact hole 185a and a second contact hole 185b that expose the first drain electrode 175a and the second drain electrode 175b are formed in the first passivation layer 180p and the second passivation layer 180q.

A third contact hole 185c that exposes a portion of the reference electrode 137 and a portion of the third drain electrode 175c is formed in the first passivation layer 180p, the second passivation layer 180q, and the gate insulating layer 140. The third contact hole 185c is covered by a connecting member 195. The connecting member 195 electrically connects the reference electrode 137 and the third drain electrode 175c exposed through the third contact hole 185c.

A plurality of pixel electrodes 191 is formed on the second passivation layer 180q. Each of the pixel electrodes 191 includes a first sub-pixel electrode 191a and a second sub-pixel electrode 191b that are spaced apart from each other with the gate line 121 included therebetween. The sub-pixel electrodes 191a and 191b are adjacent to each other in a column direction with respect to the gate line 121. The pixel electrodes 191 may be formed of a transparent conductive material such as indium tin oxide ("ITO"), indium zinc oxide ("IZO") or the like, or a reflective metal such as aluminum, silver, chromium, or an alloy thereof.

The first sub-pixel electrode 191a and the second sub-pixel electrode 191b each include a basic electrode as illustrated in FIG. 5 or alternatively, at least one electrode modified based on the basic electrode.

The first sub-pixel electrode 191a and the second sub-pixel electrode 191b are respectively physically and electrically connected to the first drain electrode 175a and the second drain electrode 175b via the first contact hole 185a and the second contact hole 185b, and receive a data voltage from the first drain electrode 175a and the second drain electrode 175b. Here, a portion of the data voltage applied to the second drain electrode 175b is divided by the third source electrode 173c so that a voltage applied to the first sub-pixel electrode 191a is greater than a voltage applied to the second sub-pixel electrode 191b.

The first sub-pixel electrode 191a and the second sub-pixel electrode 191b, to which the data voltage is applied, generate an electrical field with the common electrode 270 of the upper display panel 200 so as to determine a direction of the liquid crystal molecules 31 of the liquid crystal layer 3 between the two electrodes 191 and 270. Luminance of light that passes through the liquid crystal layer 3 is varied according to a direction of liquid crystal molecules that is determined as described above.

A lower alignment layer 11 is coated on the pixel electrode 191.

Next, a basic electrode 199 will be described with reference to FIG. 4.

Figure 4:
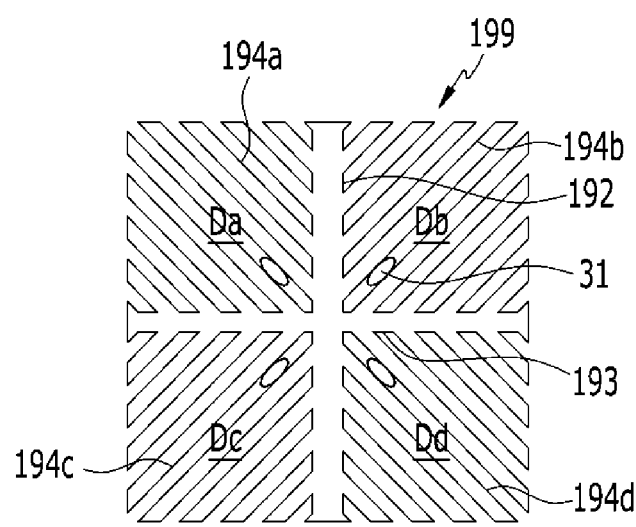
FIG. 4 is a top plan view of an exemplary embodiment of a basic region of a pixel electrode in a lower panel according to the present invention.

As shown in FIG. 4, the overall shape of the basic electrode 199 is a quadrangle, and includes a cross-shaped stem having a transverse stem 193 and a longitudinal stem 192 that are crossed. Further, the basic electrode 199 is divided into a first subregion Da, a second subregion Db, a third subregion Dc, and a fourth subregion Dd by the horizontal stem portion 193 and the vertical stem portion 192, and each of the subregions Da to Dd includes a plurality of first fine branch portions 194a, a plurality of second fine branch portions 194b, a plurality of third fine branch portions 194c, and a plurality of fourth fine branch portions 194d.

The first fine branch portions 194a extend obliquely in an upper left direction from the horizontal stem portion 193 or the vertical stem portion 192, and the second fine branch portions 194b extend obliquely in an upper right direction from the horizontal stem portion 193 or the vertical stem portion 192. Further, the third fine branch portions 194c extend in a lower left direction from the horizontal stem portion 193 or the vertical stem portion 192, and the fourth fine branch portions 194d extend obliquely in a lower right direction from the horizontal stem portion 193 or the vertical stem portion 192.

The first to fourth fine branch portions 194a, 194b, 194c, and 194d form an angle of approximately 45° or 135° with gate lines 121a and 121b or the horizontal stem portion 193. Further, the fine branch portions 194a, 194b, 194c, and 194d of the two adjacent subregions Da, Db, Dc, and Dd may be positioned orthogonal to each other.

The width of the fine branch portions 194a, 194b, 194c, and 194d may be in the range of about 2.5 to about 5.0 micrometers (μm) and the gap between the adjacent fine branch portions 194a, 194b, 194c, and 194d in one of the subregions Da, Db, Dc, or Dd may be in the range of about 2.5 to about 5.0 μm.

According to another exemplary embodiment, the widths of the fine branch portions 194a, 194b, 194c, and 194d may be increased to be closer to the horizontal stem portion 193 or the vertical stem portion 192, and a difference between the width of the widest portion and the width of the narrowest portion in one of the fine branch portions 194a, 194b, 194c, or 194d may be in the range of about 0.2 to about 1.5 μm.

The first subpixel electrode 191a and the second subpixel electrode 191b are connected to the first drain electrode 175a and the second drain electrode 175b through the first contact hole 185a and the second contact hole 185b, respectively, and receive the data voltage from the first drain electrode 175a and the second drain electrode 175b, respectively. In this case, sides of the first to the fourth fine branch portions 194a, 194b, 194c, and 194d distort the electric field and makes a horizontal component of the electric field that determines the inclination direction of the liquid crystal molecules 31. The horizontal component of the electric field is substantially horizontal to the sides of the first to fourth fine branch portions 194a, 194b, 194c, and 194d. Accordingly, as illustrated in FIG. 4, the liquid crystal molecules 31 are inclined in a direction parallel to the longitudinal direction of the fine branch portions 194a, 194b, 194c, and 194d. Since one basic electrode 199 includes four subregions Da to Dd, in which longitudinal directions of the fine branch portions 194a, 194b, 194c, and 194d are different from each other, the liquid crystal molecules 31 are inclined in about four different directions, and four domains, in which the alignment direction of the liquid crystal molecules 31 differ from each other, are formed in the liquid crystal layer 3. As described above, when the inclination direction of the liquid crystal molecules is diversified, a reference viewing angle of the liquid crystal display is increased.

Hereinafter, the upper panel 200 will be described.

Referring to FIG. 2 and FIG. 3, a black matrix 220 is formed on the insulation substrate 210. The black matrix 220 is formed on the upper panel 220 to correspond to a region of the lower panel 100 in which the data lines are formed and a region in which transistors or the like are formed.

An overcoat layer 250 is formed on the black matrix 220. The overcoat layer 250 may be omitted.

The common electrode 270 is formed on the overcoat layer 250. An upper alignment layer 21 is formed on the common electrode 270.

The liquid crystal layer 3 is formed between the lower panel 100 and the upper panel 200. Now, the liquid crystal layer 3 including an exemplary embodiment of the liquid crystal composition according to the present invention will be described.

The liquid crystal layer 3 includes a liquid crystal composition including one or more compound represented by Chemical Formula 1.

[Chemical Formula 1]

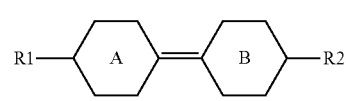

In Chemical Formula 1,

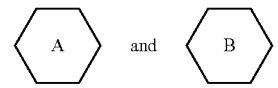

are cyclohexane or tetrahydropyran.

In Chemical Formula 1, R1 and R2 are each independently hydrogen, a C1 to C8 alkyl group, a C2 to C8 alkenyl group, or a C1 to C8 alkoxy group.

Also, a hydrogen in

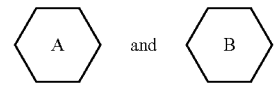

may be substituted with F, and —CH$_2$— group in

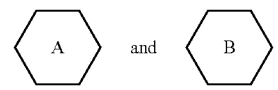

may be substituted with one of —O— or —CF$_2$—.

In Chemical Formula 1, one or more hydrogen in R1 and R2 may be substituted with F, one or more —CH$_2$— group in R1 and R2 may be substituted with —OCH$_2$—, —CF$_2$—, or —OCF$_2$—, or one or more —CH$_3$ group in R1 and R2 may be substituted with —CF$_3$ or —OCF$_3$.

The compound of Chemical Formula 1 may be selected from Chemical Formula 1-1 to Chemical Formula 1-9.

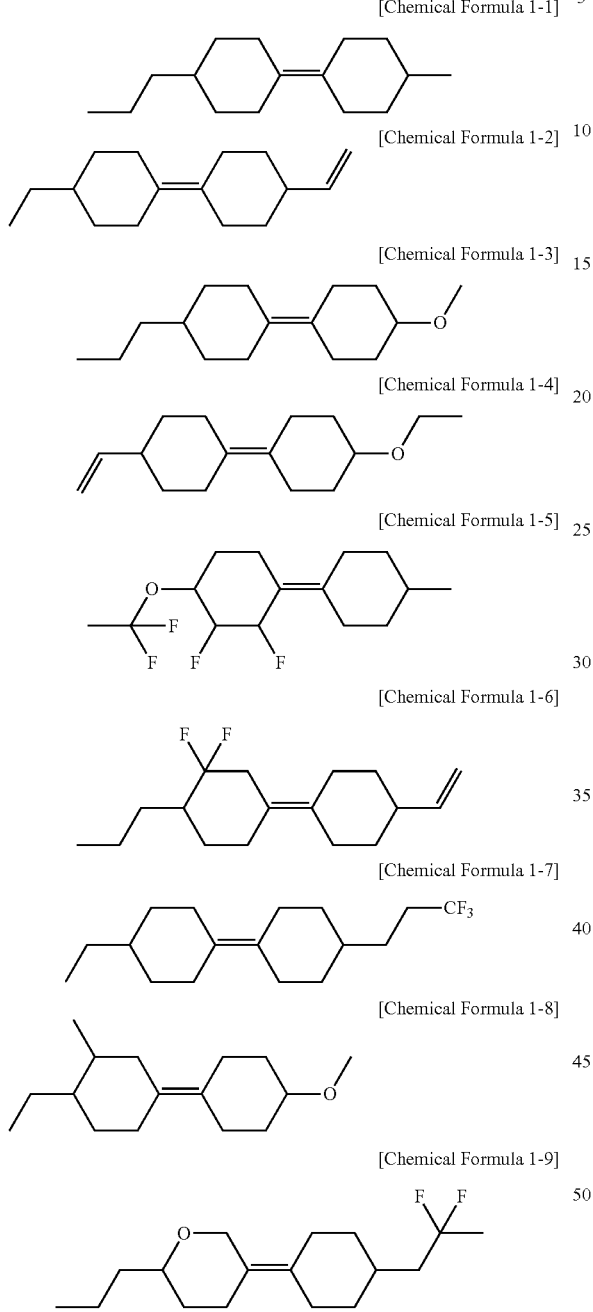

[Chemical Formula 1-1]
[Chemical Formula 1-2]
[Chemical Formula 1-3]
[Chemical Formula 1-4]
[Chemical Formula 1-5]
[Chemical Formula 1-6]
[Chemical Formula 1-7]
[Chemical Formula 1-8]
[Chemical Formula 1-9]

In an exemplary embodiment, the liquid crystal composition of the liquid crystal layer of the liquid crystal display may additionally include at least one compound selected from Chemical Formulas 2-1 to 2-8.

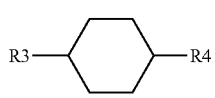

[Chemical Formula 2-1]

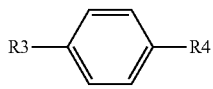

[Chemical Formula 2-2]

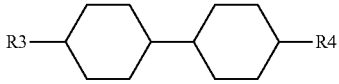

[Chemical Formula 2-3]

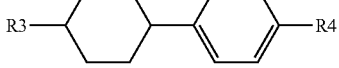

[Chemical Formula 2-4]

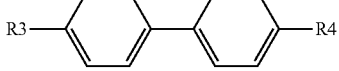

[Chemical Formula 2-5]

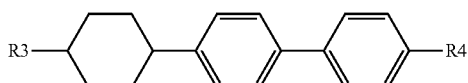

[Chemical Formula 2-6]

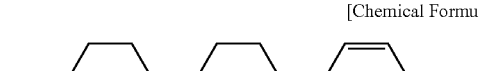

[Chemical Formula 2-7]

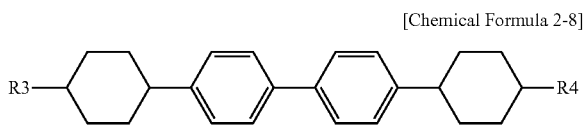

[Chemical Formula 2-8]

In Chemical Formulas 2-1 to 2-8, R3 and R4 are independently hydrogen, a C1 to C8 alkyl group, a C2 to C8 alkenyl group, or a C1 to C8 alkoxy group.

A hydrogen included in R3 and R4 may be substituted with F, a —CH2— group in R3 and R4 may be substituted with —OCH2—, —CF2—, or —OCF2—, or a —CH3 group in R3 and R4 may be substituted with —CF3 or —OCF3.

Also, in the liquid crystal composition of the liquid crystal layer of the present invention, the compound of Chemical Formula 2-1 to 2-8 may be present in an amount of about 2 wt % to about 40 wt % based on the entire weight of the liquid crystal composition.

In an exemplary embodiment, the liquid crystal composition of the liquid crystal layer may additionally include at least one compound selected from Chemical Formulas 3-1 to 3-12.

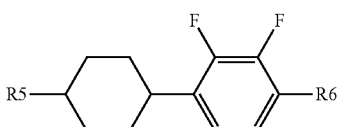

[Chemical Formula 3-1]

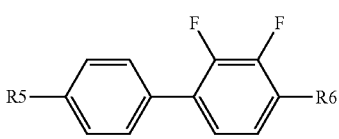

[Chemical Formula 3-2]

[Chemical Formula 3-3]

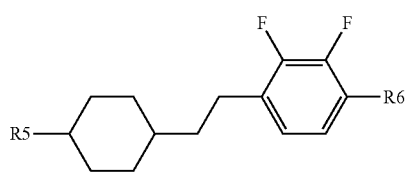

[Chemical Formula 3-4]

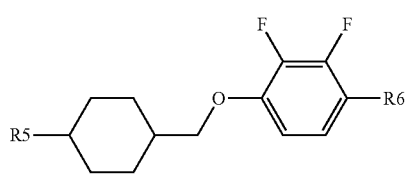

[Chemical Formula 3-5]

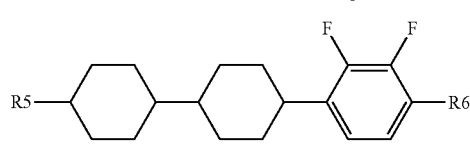

[Chemical Formula 3-6]

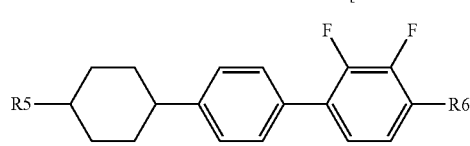

[Chemical Formula 3-7]

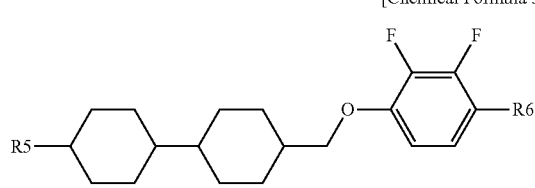

[Chemical Formula 3-8]

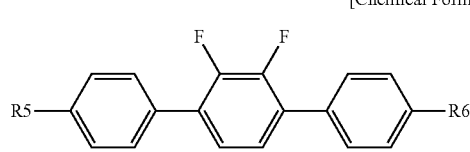

[Chemical Formula 3-9]

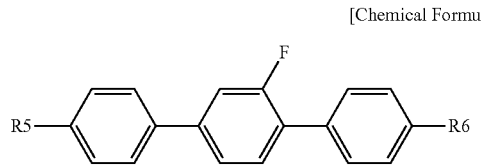

[Chemical Formula 3-10]

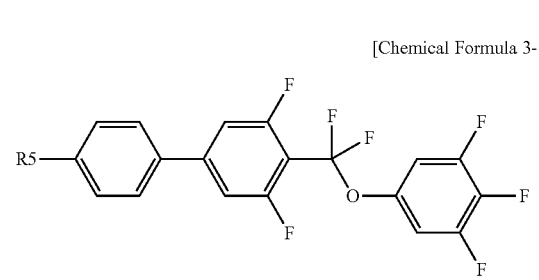

[Chemical Formula 3-11]

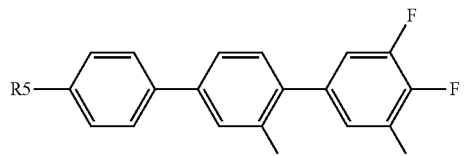

[Chemical Formula 3-12]

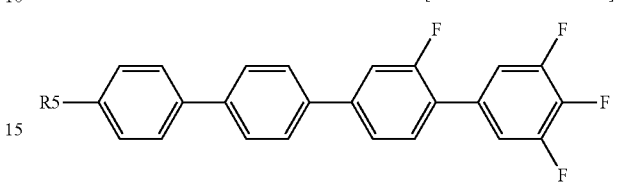

In Chemical Formulas 3-1 to 3-12, R5 and R6 are independently hydrogen, a C1 to C8 alkyl group, a C2 to C8 alkenyl group, or a C1 to C8 alkoxy group.

Also, at least one hydrogen included in R5 and R6 may be substituted with fluorine.

In an exemplary embodiment, the compound selected from Chemical Formulas 3-1 to 3-12 may be present in an amount of about 2 wt % to about 30 wt % based on the entire weight of the liquid crystal composition.

As such, for the liquid crystal display including the compound represented by Chemical Formula 1 within the liquid crystal layer, the rotational viscosity of the liquid crystal layer is low compared to the conventional liquid crystal display, thereby improving the response speed of the liquid crystal display.

The liquid crystal display having the structure illustrated in FIG. 1 to FIG. 4 is only one example and the exemplary liquid crystal composition according to the present invention may be clearly applied to other liquid crystal displays, without being limited to only the vertical alignment (VA) mode liquid crystal display in which the pixel electrode is positioned in the first display panel and the common electrode is positioned in the second display panel.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A liquid crystal composition comprising:
one or more compound represented by Chemical Formula 1:

[Chemical Formula 1]

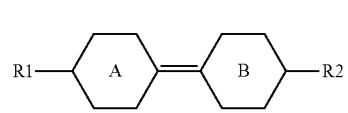

wherein,

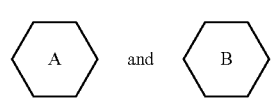

are independently a cyclohexane or a tetrahydropyran, or

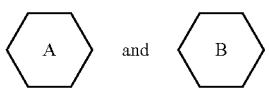

are independently a substituted cyclohexane or a substituted tetrahydropyran, in which one or more hydrogen is substituted with F, or one or more —CH$_2$—group is substituted with —O— or —CF$_2$, and R1 is a C1 to C8 alkyl group, a C2 to C8 alkenyl group, a C1 to C8 alkoxy group, a substituted C1 to C8 alkyl group, a substituted C2 to C8 alkenyl group, or a substituted C1 to C8 alkoxy group, in which one or more hydrogen is substituted with F, one or more —CH$_2$— group is substituted with —OCH$_2$—, —CF$_2$—, or —OCF$_2$—, or one or more —CH$_3$ group is substituted with —CF$_3$ or —OCF$_3$, and R2 is a C2 to C8 alkenyl group, a C1 to C8 alkoxy group, a substituted C1 to C8 alkyl group, a substituted C2 to C8 alkenyl group, or a substituted C1 to C8 alkoxy group, in which one or more hydrogen is substituted with F, one or more —CH$_2$— group is substituted with —OCH$_2$—, —CF$_2$—, or —OCF$_2$—, or one or more —CH$_3$ group is substituted with —CF$_3$ or —OCF$_3$, or R1 is a substituted C1 to C8 alkoxy group in which one or more hydrogen is substituted with F and R2 is a C1 to C8 alkyl group, and at least one compound selected from Chemical Formulas 2-1 to 2-8:

[Chemical Formula 2-1]

[Chemical Formula 2-2]

[Chemical Formula 2-3]

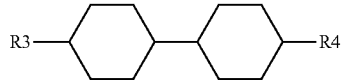

[Chemical Formula 2-4]

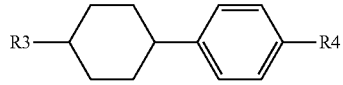

[Chemical Formula 2-5]

[Chemical Formula 2-6]

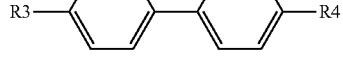

[Chemical Formula 2-7]

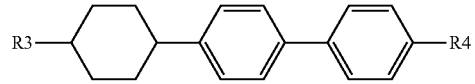

[Chemical Formula 2-8]

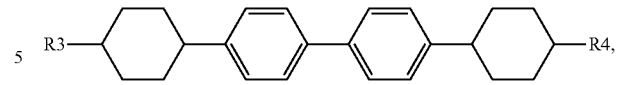

wherein, R3 and R4 are independently hydrogen, a C1 to C8 alkyl group, a C2 to C8 alkenyl group, or a C1 to C8 alkoxy group, or wherein R3 and R4 are a substituted C1 to C8 alkyl group, a substituted C2 to C8 alkenyl group, or a substituted C1 to C8 alkoxy group in which one or more hydrogen is substituted with F, one or more —CH$_2$— group is substituted with —OCH$_2$—, —CF$_2$—, or —OCF$_2$—, or one or more —CH$_3$ group is substituted with —CF$_3$ or —OCF$_3$.

2. The liquid crystal composition of claim 1, wherein:

the compound represented by Chemical Formula 1 is at least one compound selected from Chemical Formulas 1-2 to 1-9:

[Chemical Formula 1-2]

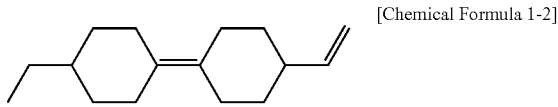

[Chemical Formula 1-3]

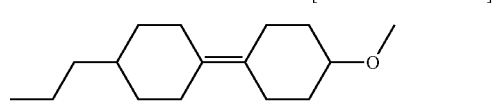

[Chemical Formula 1-4]

[Chemical Formula 1-5]

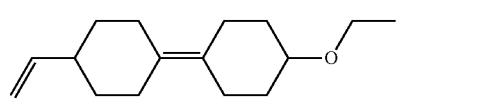

[Chemical Formula 1-6]

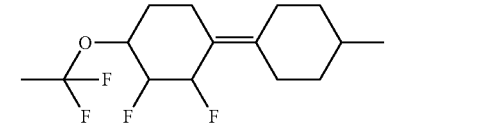

[Chemical Formula 1-7]

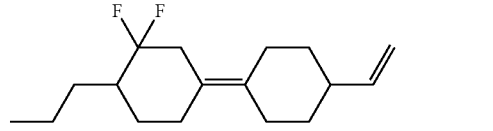

[Chemical Formula 1-8]

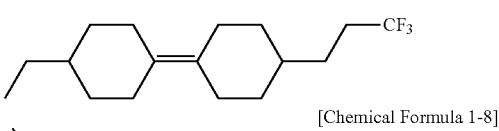

[Chemical Formula 1-9]

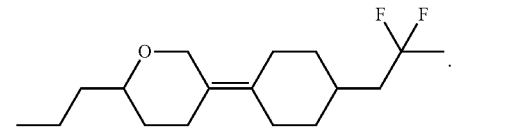

3. The liquid crystal composition of claim 1, wherein:

the compound represented by Chemical Formula 1 is present in an amount of about 1 wt % to about 40 wt % based on the entire weight of the liquid crystal composition.

4. The liquid crystal composition of claim 1, wherein:

the compound selected from Chemical Formulas 2-1 to 2-8 is present in an amount of about 2 wt % to about 40 wt %, based upon the entire weight of the liquid crystal composition.

5. The liquid crystal composition of claim 1, wherein:

the liquid crystal composition further comprises at least one compound selected from Chemical Formulas 3-1 to 3-12:

[Chemical Formula 3-1]
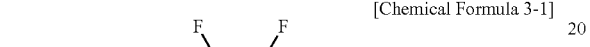

[Chemical Formula 3-2]
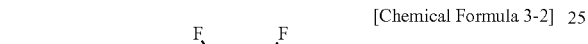

[Chemical Formula 3-3]

[Chemical Formula 3-4]
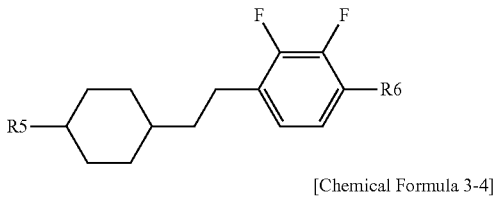

[Chemical Formula 3-5]
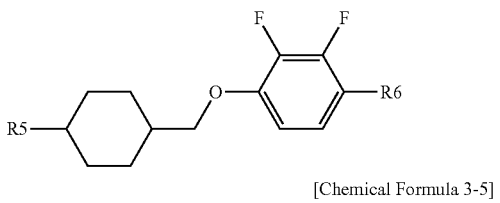

[Chemical Formula 3-6]
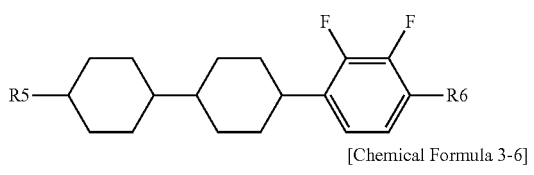

[Chemical Formula 3-7]
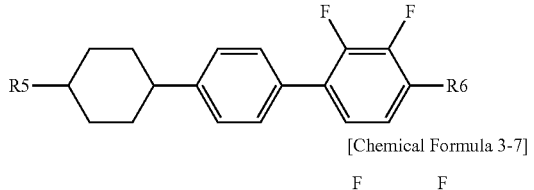

[Chemical Formula 3-8]
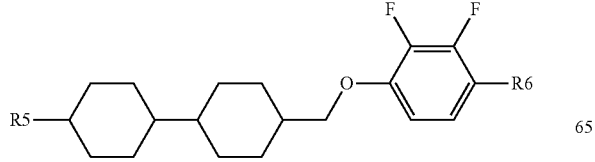

-continued

[Chemical Formula 3-9]
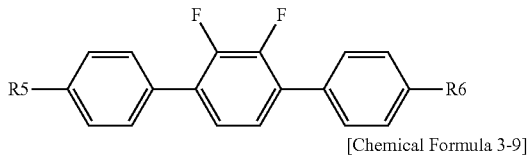

[Chemical Formula 3-10]
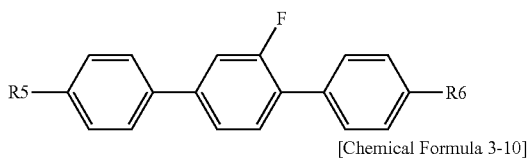

[Chemical Formula 3-11]
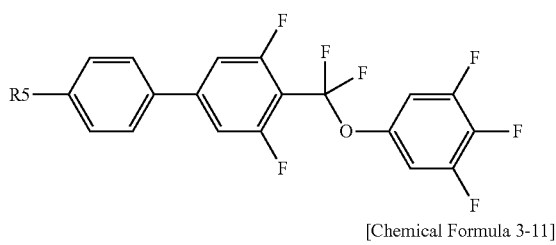

[Chemical Formula 3-12]
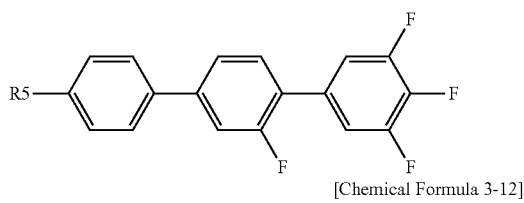

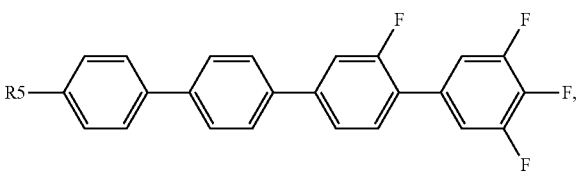

wherein, R5 and R6 are independently hydrogen, a C1 to C8 alkyl group, a C2 to C8 alkenyl group, or a C1 to C8 alkoxy group, or R5 and R6 are independently hydrogen a substituted a C1 to C8 alkyl group, a substituted C2 to C8 alkenyl group, or a substituted C1 to C8 alkoxy group, in which at least one hydrogen in R5 and R6 is substituted with fluorine.

6. The liquid crystal composition of claim 5, wherein:

the compound selected from Chemical Formulas 3-1 to 3-12 is present in an amount of about 2 wt % to about 30 wt % based upon the entire liquid crystal composition.

7. A liquid crystal display comprising:

a first insulation substrate comprising a pixel electrode;

a second insulation substrate facing the first insulation substrate and comprising a common electrode; and a liquid crystal layer positioned between the first insulation substrate and the second insulation substrate, wherein the liquid crystal layer comprises one or more compound represented by Chemical Formula 1:

[Chemical Formula 1]
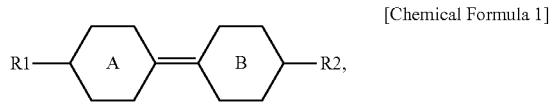

wherein,

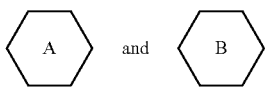

are independently a cyclohexane or tetrahydropyran, or

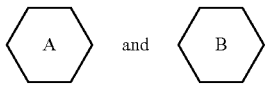

are independently a substituted cyclohexane or substituted tetrahydropyran, in which one or more hydrogen is substituted with F, or one or more —CH$_2$— group is substituted with —O— or —CF$_2$ and
  R1 and R2 are independently hydrogen, a C1 to C8 alkyl group, a C2 to C8 alkenyl group, or a C1 to C8 alkoxy group, or R1 and R2 are independently a substituted C1 to C8 alkyl group, a substituted C2 to C8 alkenyl group, or a substituted C1 to C8 alkoxy group, in which one or more hydrogen is substituted with F, one or more —CH$_2$— group is substituted with —OCH$_2$—, —CF$_2$—, or —OCF$_2$—, or one or more —CH$_3$ group is substituted with —CF$_3$ or —OCF$_3$.

8. The liquid crystal display of claim 7, wherein:
  the compound represented by Chemical Formula 1 is at least one compound selected from Chemical Formulas 1-1 to 1-9:

[Chemical Formula 1-1]

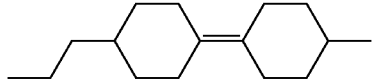

[Chemical Formula 1-2]

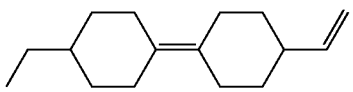

[Chemical Formula 1-3]

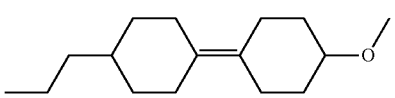

[Chemical Formula 1-4]

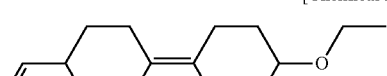

[Chemical Formula 1-5]

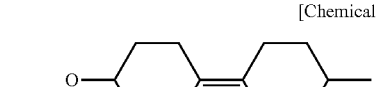

[Chemical Formula 1-6]

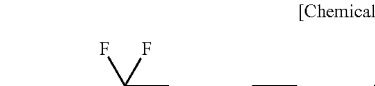

[Chemical Formula 1-7]

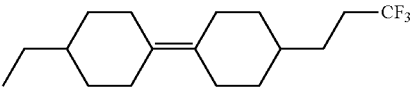

[Chemical Formula 1-8]

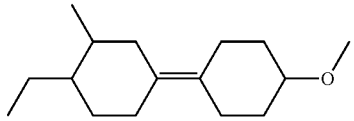

[Chemical Formula 1-9]

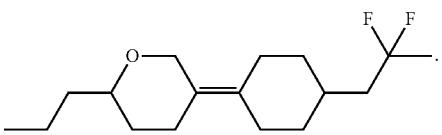

9. The liquid crystal display of claim 7, wherein:
  the compound represented by Chemical Formula 1 is present in an amount of about 1 wt % to about 40 wt % based upon the entire weight of the liquid crystal composition.

10. The liquid crystal display of claim 7, wherein:
  the liquid crystal layer further comprises at least one compound selected from Chemical Formulas 2-1 to 2-8:

[Chemical Formula 2-1]

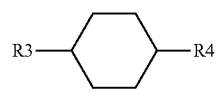

[Chemical Formula 2-2]

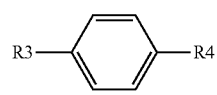

[Chemical Formula 2-3]

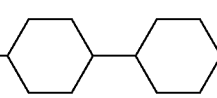

[Chemical Formula 2-4]

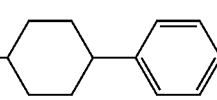

[Chemical Formula 2-5]

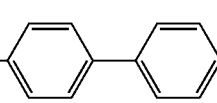

[Chemical Formula 2-6]

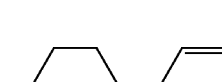

[Chemical Formula 2-7]

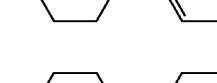

[Chemical Formula 2-8]

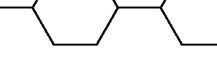

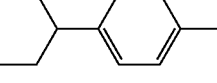

wherein, R3 and R4 are independently hydrogen, a C1 to C8 alkyl group, a C2 to C8 alkenyl group, or a C1 to C8 alkoxy group, or wherein R3 and R4 are independently a substituted C1 to C8 alkyl group, a substituted C2 to C8 alkenyl group, or a substituted C1 to C8 alkoxy group in which one or more hydrogen is substituted with F, one or more —CH$_2$— group is substituted with —OCH$_2$—, —CF$_2$—, or —OCF$_2$—, or one or more —CH$_3$ group is substituted with —CF$_3$ or —OCF$_3$.

11. The liquid crystal display of claim 10, wherein:
the compound selected from Chemical Formulas 2-1 to 2-8 is present in an amount of about 2 wt % to about 40 wt % based on the entire weight of the liquid crystal composition.

12. The liquid crystal display of claim 7, wherein:
the liquid crystal layer further comprises at least one compound selected from Chemical Formulas 3-1 to 3-12:

[Chemical Formula 3-1]
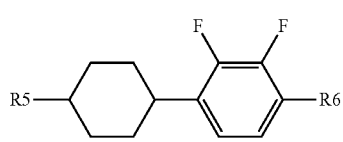

[Chemical Formula 3-2]
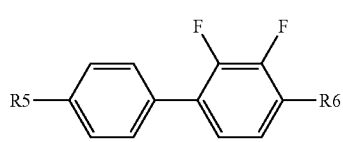

[Chemical Formula 3-3]
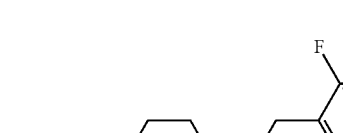

[Chemical Formula 3-4]
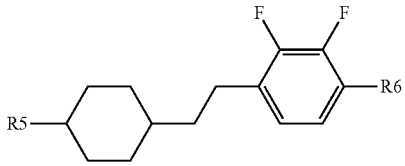

[Chemical Formula 3-5]
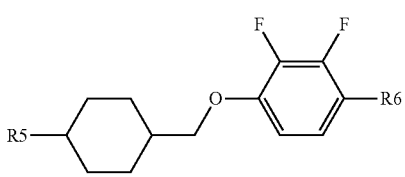

[Chemical Formula 3-6]
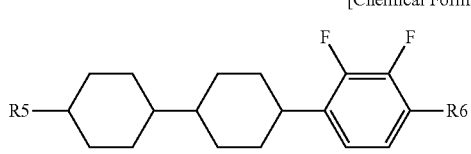

[Chemical Formula 3-7]
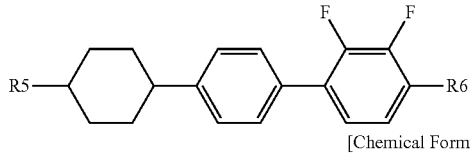

[Chemical Formula 3-8]
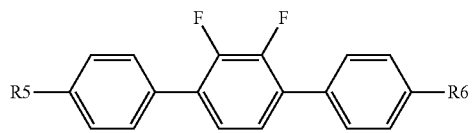

[Chemical Formula 3-9]
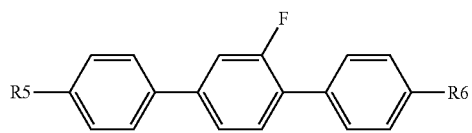

[Chemical Formula 3-10]
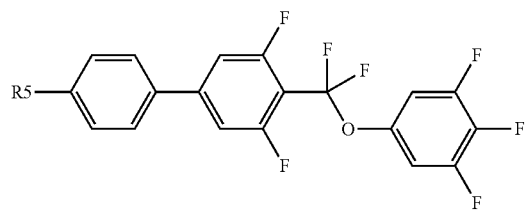

[Chemical Formula 3-11]
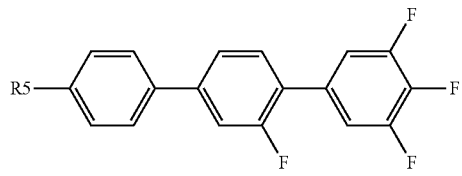

[Chemical Formula 3-12]
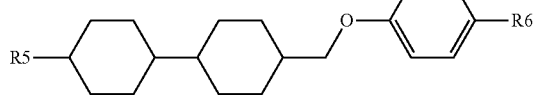

wherein, R5 and R6 are independently hydrogen, a C1 to C8 alkyl group, a C2 to C8 alkenyl group, or a C1 to C8 alkoxy group, or R5 and R6 are independently a substituted C1 to C8 alkyl group, a substituted C2 to C8 alkenyl group, or a substituted C1 to C8 alkoxy group, in which at least one hydrogen in R5 and R6 is substituted with fluorine.

13. The liquid crystal display of claim 12, wherein:
the compound of Chemical Formula 3-1 to 3-12 is present in an amount of about 2 wt % to about 30 wt % based upon the entire weight of the liquid crystal composition.

14. The liquid crystal display of claim 7, wherein:
the pixel electrode comprises a cross-shape stem and a minute branch extending from the cross-shape stem in 4 diagonal directions.

* * * * *